US012656257B2

(12) United States Patent
Vamerali et al.

(10) Patent No.: US 12,656,257 B2
(45) Date of Patent: Jun. 16, 2026

(54) METHOD AND DEVICE FOR THE RAPID QUANTIFICATION OF AFLATOXIN M1 (AFM1) IN MILK

(71) Applicant: UNIVERSITA' DEGLI STUDI DI PADOVA, Padua (IT)

(72) Inventors: Teofilo Vamerali, Quinto Vicentino (IT); Giuseppe Barion, Rovigo (IT); Stefano Tiozzo Netti, Sottomarina (IT)

(73) Assignee: UNIVERSITA' DEGLI STUDI DI PADOVA, Padua (IT)

( * ) Notice: Subject to any disclaimer, the term of this patent is extended or adjusted under 35 U.S.C. 154(b) by 771 days.

(21) Appl. No.: 17/906,911

(22) PCT Filed: Mar. 23, 2021

(86) PCT No.: PCT/IB2021/052371
§ 371 (c)(1),
(2) Date: Sep. 21, 2022

(87) PCT Pub. No.: WO2021/191779
PCT Pub. Date: Sep. 30, 2021

(65) Prior Publication Data

US 2023/0126620 A1 Apr. 27, 2023

(30) Foreign Application Priority Data

Mar. 26, 2020 (IT) ........................ 102020000006370

(51) Int. Cl.
*G01N 21/64* (2006.01)
*G01N 33/04* (2006.01)

(52) U.S. Cl.
CPC ......... *G01N 21/6486* (2013.01); *G01N 33/04* (2013.01); *G01N 2021/6421* (2013.01); *G01N 21/645* (2013.01)

(58) Field of Classification Search
CPC ........ G01N 33/04; G01N 33/14; G01N 21/64; G01N 21/6486; G01N 21/645;
(Continued)

(56) References Cited

U.S. PATENT DOCUMENTS 4,285,698 A * 8/1981 Otto ........................ G01N 30/06 250/910
4,535,248 A * 8/1985 Schade .............. G01N 21/6486 250/910

(Continued)

FOREIGN PATENT DOCUMENTS

EP 2270475 A1 * 1/2011

OTHER PUBLICATIONS

Cheema et al. Proc. of SPIE, vol. 11979, 2022, pp. 1197904-1 to 1197904-4.*
Lee et al. Food Control, vol. 50, Sep. 20, 2014, pp. 467-471.*
Stubblefield, R. J. Assoc. Off. Anal. Chem., vol. 70, No. 6, 1987, pp. 1047-1049.*

(Continued)

*Primary Examiner* — Maureen Wallenhorst
(74) *Attorney, Agent, or Firm* — Silvia Salvadori, P.C.; Silvia Salvadori

(57) ABSTRACT

A device and its use for the direct quantification of Aflatoxin M1 (AFM1) in a sample of milk, the use includes a) providing a sample of milk; b) irradiating the sample of milk of step a) with a first electromagnetic radiation which includes at least one wavelength in a range from 340 to 400 nm; c) detecting a second electromagnetic radiation, emitted by the sample of milk of step b), in a range from 410 to 860 nm; d) selecting at least 9 wavelengths in a range from 410 to 860 nm of the second electromagnetic radiation detected in step c); and e) quantifying the Aflatoxin M1 (AFM1) in the sample of milk, on the basis of an intensity of the radiation emitted by the wavelengths selected in step d).

17 Claims, 3 Drawing Sheets

(58) Field of Classification Search
CPC .......... G01N 2021/6421; Y10T 436/20; Y10T 436/203332
USPC ..... 436/20, 22, 23, 127, 131, 164, 165, 172; 422/82.05, 82.08, 554
See application file for complete search history.

(56) References Cited

U.S. PATENT DOCUMENTS

| | | | | |
|---|---|---|---|---|
| 2007/0117219 A1* | 5/2007 | Zabe | B01D 15/3809 | 436/514 |
| 2007/0142678 A1* | 6/2007 | Losso | A23L 33/105 | 568/824 |
| 2009/0255473 A1* | 10/2009 | Katz | A23C 19/02 | 119/14.08 |
| 2021/0132058 A1* | 5/2021 | Li | G01N 33/577 | |

OTHER PUBLICATIONS

Hashemi et al. Spectrochimica Acta Part A: Molecular and Biomolecular Spectroscopy, vol. 128, Mar. 4, 2014, pp. 583-590.*

Gregory III et al. J. Assoc. Off. Anal. Chem., vol. 64, No. 1, 1981, pp. 144-151.*

Mignani A.G. et al., “Optical fiber fluorescence spectroscopy for detecting AFM1 in milk”, Proceedings of Spie vol. 7004, Apr. 14, 2008, p. 70045S.

Ru-Dong W. et al., “Aflatoxin-solvent interactions induced by ultraviolet light”, Journal of the Association of Official Analytical Chemists, vol. 56, No. 6, Nov. 1, 1973, pp. 1425-1430.

Search Report and Written Opinion of PCT/IB2021/052371 of May 11, 2021.

Shuib N. S. et al., “Determination of aflatoxin M1 in milk and dairy products using high performance liquid chromatography-fluorescence with post column photochemical derivatization”, Journal of Chromatography A vol. 1510 , Jun. 19, 2017, pp. 51-56.

* cited by examiner

METHOD AND DEVICE FOR THE RAPID QUANTIFICATION OF AFLATOXIN M1 (AFM1) IN MILK

FIELD OF THE INVENTION

The present invention relates to a rapid method for the direct quantification of Aflatoxin M1 (AFM1) in a sample of milk. The invention further relates to a device to be used in said method.

BACKGROUND

Aflatoxin B1 (AFB1) is considered the most carcinogenic/genotoxic mycotoxin known, produced by toxigenic fungal strains of *Aspergillus flavus, Aspergillus* nominus and *Aspergillus parasiticus*, which accumulates in plant raw materials under certain conditions of humidity and high temperatures, being these conditions increasingly frequent in recent years due to climate change (Battilani et al., "Aflatoxin B1 contamination in maize in Europe increases due to climate change", Scientific Reports, 6, 24328). AFB1, if ingested by dairy farm animals (cattle, sheep, goats, buffaloes, etc.) through food, is converted in the liver into Aflatoxin M1 (AFM1) by hydroxylation, and then discharged into milk. Recently, it has been documented that AFM1 is carcinogenic to liver cells (Muriel et al., "The liver: general aspects and epidemiology", Liver Pathophysiology, pages 3-22, Academic Press, 2017). The mutagenic action of Aflatoxin B1 and M1 is linked to the formation of epoxide, a metabolic intermediate that forms covalent bonds with the DNA chain. Damages to the immune system, on the other hand, have been demonstrated in vivo in laboratory guinea pigs exposed to 25-50 μg $kg^{-1}$ live weight of maize Aflatoxins (Kobra Shirani et al., "Immunotoxicity of aflatoxin M1: as a potent suppressor of innate and acquired immune systems in a subacute study", J Sci Food Agric., 98(15), 2018, pages 5884-5892). Immunosuppressive effects have not yet been verified in humans, but the actual carcinogenic potential of Aflatoxins has been focused on (Evan Gallagher et al., "Mechanisms of aflatoxin carcinogenesis", Ann. Rev. Pharmacol., 34, 1994, pages 135-172). Aflatoxin M1 (AFM1) is considered the most important Aflatoxin in milk, and the European Union has set a very restrictive maximum limit (50 ppt, ng $kg^{-1}$ of milk). This is currently the lowest legal limit worldwide, an order of magnitude lower than the 500 ppt limit set by the Food and Drug Administration (FDA) and adopted in the USA (US Food and Drug Administration, 1996, Sec. 527.400 Whole milk, low fat milk, skim milk-aflatoxin M1 (CPG 7106.210). FDA compliance policy guides. FDA, Washington, DC, 219).

At present, a number of methods are available for the detection and quantification of Aflatoxin M1 (AFM1).

The most widely used prior method for the quantification of Aflatoxin M1 (AFM1) (Mortimer et al., "Rapid and highly sensitive analysis of aflatoxin M1 in liquid and powdered milks using an affinity column cleanup", Journal of Chromatography, 407, 393-398, 1987) is based on determination by HPLC (High Pressure Liquid Chromatography) coupled with a fluorimetric sensor. This method requires several stages of preliminary purification and pre-treatment of the sample of milk to be analyzed, given the complexity of the chemical composition of the milk itself and the presence within it of a wide variety of chemical species that generate interferences in the fluorimetric measurement due to additional peaks of emission and superimposed on the peak of Aflatoxin M1. Because of these unavoidable interferences, the Mortimer's method involves degreasing by centrifugation and filtration of the sample, followed by extraction/elution with immunoaffinity columns and special organic solvents (methanol) of Aflatoxin M1, and finally concentration under nitrogen flow and resuspension in a mixture of acetonitrile and water, to obtain the sample for chromatographic analysis (HPLC). The final quantification of Aflatoxin AFM1 is performed by means of a calibration curve obtained with standards of known concentration of Aflatoxin AFM1.

A second known method involves the use of HPLC coupled to mass sensor (triple quadrupole) (Espenschied et al., 2015, "Sensitive and Fast Analysis of Aflatoxin M1 in Milk at Picogram Levels using LC-MS/MS". Analysis and Sample Preparation using Interference Removal Solid Phase Extraction, Sigma-Aldrich). Similarly to Mortimer's method, this second method also requires a careful preparation of the sample, through phases of degreasing, filtration, toxin extraction with immunoaffinity columns. The detection of Aflatoxin AFM1, subsequent to pre-treatments, is performed by recognition of molecular fragments of the toxin obtained through the application of strong electromagnetic fields and the subsequent quantification is performed by estimating the abundance of the identified molecular fragments.

In order for the peaks in the LC-MS graph to be easily identifiable and distinct from each other, an SPE (Solid Phase Extraction, e.g. by "Supe) Tox AflaZea, Sigma-Aldrich") step is required, which allows the removal of interference and the detection of only the analyte of interest.

An additional known method that allows a quantification of Aflatoxin AFM1 is the ELISA test (or Lateral Flow test) (Imtiaz and Yunus, "Comparison of some ELISA kits for Aflatoxin M1 quantification", Journal of AOAC International, 102 (2), 677-679, 2019). This method is based on the reaction of the toxin with an antibody and an antibody conjugate (to an enzyme phosphatase, generally) which, in the presence of the enzyme substrate, generates a staining intensity proportional to the abundance of Aflatoxin AFM1. Photometric reading of the staining intensity allows the quantification of Aflatoxin AFM1.

In this case, similar to the previous ones, not only does the measurement require toxin extraction steps, but it also involves costs of the reagents and instrumentation used. The ELISA test is faster than methodologies using HPLC, but provides a lower detection rate and lower measurement accuracy.

Therefore, the Applicant has noted that the methods for the quantification of Aflatoxin M1 (AFM1) in milk according to the prior art have multiple technical and application limitations.

In particular, in light of the complexity of the chemical composition of a raw and non-pretreated sample of milk, the methods according to the prior art necessarily require the execution of long and complex separation, purification and pre-treatment steps in order to isolate the toxin from the sample before its subsequent quantification.

Consequently, these methods by their nature require long analysis and preparation times (e.g. due to the elution time of the analyte to be detected), extreme care in identifying and eliminating interferences due to the presence of other components present in the sample under analysis, and high costs due to the complex instrumentation required, the solvents to be used and the specialised personnel to be employed.

Moreover, the presence in said known methods of several steps of washing, elution, degreasing, filtration, extraction performed with different chemical solvents, produces an accumulation of chemical waste to be disposed of. This is a further limitation of the methods of the prior art, to the detriment of their cost-effectiveness and environmental sustainability due to the need to dispose of spent reagents.

Consequently, it is still felt the need for methods for the quantification of Aflatoxin M1 (AFM1) in a sample of milk which are versatile, simple, fast and inexpensive and which are able to determine the content in that sample at concentrations which are relevant in view of the current legislation on the matter referred to above.

In fact, the Applicant noted that it is important to overcome the limitations of known analytical techniques, such as long analysis times, their complexity, sensitivity, and the cost of reagents and instrumentation and consequently their impracticality, as well as the generation of waste (plastic, chemical).

Therefore, in view of the limitations of known techniques, the primary object of the present invention is to provide a simple method, convenient in terms of cost and time required to perform the analysis, which therefore allows the detection and quantification of Aflatoxin M1 (AFM1) in a sample of milk in a direct, rapid, accurate, precise and simple way.

The present invention also relates to a device which can implement said method.

SUMMARY OF THE INVENTION

The inventors of the present invention have surprisingly found that, through the accurate selection of at least 9 specific wavelengths, comprised in a range from 410 nm to 860 nm, emitted from a sample of milk after irradiation by an electromagnetic radiation having a wavelength in a range from 340 to 400 nm, and on the basis of the intensity of the radiation emitted at said at least specific 9 wavelengths, it is possible to directly and rapidly quantify Aflatoxin M1 (AFM1) in a sample of milk not otherwise subjected to further pre-treatment/purification, allowing a better, easier and direct quantification of said toxin in said sample of milk.

Therefore, the present invention relates in a first aspect to a method for the quantification of Aflatoxin M1 (AFM1) in milk, comprising the steps of:

a) providing a sample of milk; b) irradiating the sample of milk of step a) with a first electromagnetic radiation comprising at least one wavelength in the range from 340 to 400 nm; c) detecting a second electromagnetic radiation, emitted by the sample of milk of step b), in the range from 410 to 860 nm; d) selecting at least 9 wavelengths comprised in said range from 410 to 860 nm of the second electromagnetic radiation detected in step c); and e) quantifying the Aflatoxin M1 (AFM1) in said sample of milk, on the basis of the intensity of the radiation emitted at said at least 9 wavelengths selected in step d), wherein said at least 9 wavelengths are selected from the group consisting of 410 nm, 435 nm, 560 nm, 585 nm, 645 nm, 705 nm, 760 nm, 810 nm, and 860 nm; and wherein said at least 9 wavelengths are used to quantify Aflatoxin M1 (AFM1), by means of equation (I):

$$AFM1(ppt) = 0.0092 \times (F1)^2 + 1.0694 \times (F1) + 31.635 \quad \text{(I)}$$

wherein AFM1 (ppt) is the concentration of Aflatoxin M1 in said sample of milk in ng $kg^{-1}$, and F1 is a parameter calculated by means of equation (II):

$$F1 = 2.533 \times Is_{410nm} + -0.132 \times Is_{435nm} + 5.527 \times Is_{560nm} + 1.911 \times Is_{535nm} + 7.225 \times Is_{645nm} + -1.082 \times Is_{705nm} + -8.849 \times Is_{760nm} + -11.337 \times Is_{810nm} + 1.874 \times Is_{860nm}, \quad \text{(II)}$$

and wherein $Is_{410\ nm}$, $Is_{435\ nm}$, $Is_{560\ nm}$, $Is_{585\ nm}$, $Is_{645\ nm}$, $Is_{705\ nm}$, $Is_{760\ nm}$, $Is_{810\ nm}$, $Is_{860nm}$ are the standardized fluorescence intensity values, respectively at 410 nm, 435 nm, 560 nm, 585 nm, 645 nm, 705 nm, 760 nm, 810 nm, and 860 nm, wherein said standardized fluorescence intensity values are respectively obtained according to the following equations (III1-III9):

$$Is_{410nm} = (I_{410nm} - 52.737)/2.468 \quad \text{(III1)}$$

$$Is_{435nm} = (I_{435nm} - 52.503)/2.141 \quad \text{(III2)}$$

$$Is_{560nm} = (I_{560nm} - 24.267)/0.928 \quad \text{(III3)}$$

$$Is_{585nm} = (I_{585nm} - 14.800)/0.563 \quad \text{(III4)}$$

$$Is_{645nm} = (I_{645nm} - 13.437)/0.523 \quad \text{(III5)}$$

$$Is_{705nm} = (I_{705nm} - 18.540)/0.759 \quad \text{(III6)}$$

$$Is_{760nm} = (I_{760nm} - 20.033)/2.972 \quad \text{(III7)}$$

$$Is_{810nm} = (I_{810nm} - 24.233)/4.183 \quad \text{(III8)}$$

$$Is_{860nm} = (I_{860nm} - 12.387)/1.574 \quad \text{(III9)}$$

wherein $I_{410\ nm}$, $I_{435\ nm}$, $I_{560\ nm}$, $I_{585\ nm}$, $I_{645\ nm}$, $I_{705\ nm}$, $I_{760\ nm}$, $I_{810\ nm}$, $I_{860nm}$ are respectively the values of fluorescence intensity detected in phase c), respectively at 410 nm, 435 nm, 560 nm, 585 nm, 645 nm, 705 nm, 760 nm, 810 nm, and 860 nm.

Without being bound to any theory, and as will be evident from the following and the examples, the inventors believe that by identifying at least 9 specific wavelengths comprised in a range from 410 to 860 nm of the method of the invention, emitted by a sample of milk after irradiation with an electromagnetic radiation with a wavelength in the range from 340 to 400 nm, on the basis of the intensity of the radiation emitted at said at least 9 specific wavelengths, there is an advantageous possibility of directly and quickly identifying Aflatoxin M1 (AFM1) in a sample of milk, allowing a better and easier identification and quantification of said sample of milk.

In view of this, the present invention provides a simple method, convenient in terms of the cost and time required to perform the analysis, which allows direct, rapid, accurate, and precise quantification of Aflatoxin M1 (AFM1) in a sample of milk.

Thanks to its particular electromagnetic radiation sources, its particular spectral sensor and its particular container, the device according to the present description can realize the method of the present description.

Thanks to its particular structure, the container of the device according to the present description can be manufactured at relatively low cost, occupies small space and/or allows fast and accurate analysis of the samples of milk, which can also be divided into several portions (sub-samples) for repeated analyses by the method of the present description.

In addition, the container can be removed from its housing within the device, opened for washing and reuse, and can be provided with chambers having reflective surfaces to optimize irradiation of the samples of milk.

Preferably, the device comprises one or more electromechanical actuators and/or a programmable control unit to implement the method quickly and/or automatically. Therefore, further object of the present invention is the use of said device for determining the content of Aflatoxin AFM1 in a sample of milk, by means of the method according to the present invention.

The advantages of said use are the same and derive directly and automatically from the method of the invention and the device employed for its implementation and are therefore not repeated herein.

BRIEF DESCRIPTION OF THE DRAWINGS

Further advantages and features of the method, container and device according to the present description will be apparent to those skilled in the art from the following detailed and non-limiting description of some of their embodiments with reference to the appended drawings wherein.

DETAILED DESCRIPTION OF THE INVENTION

Figure 1:
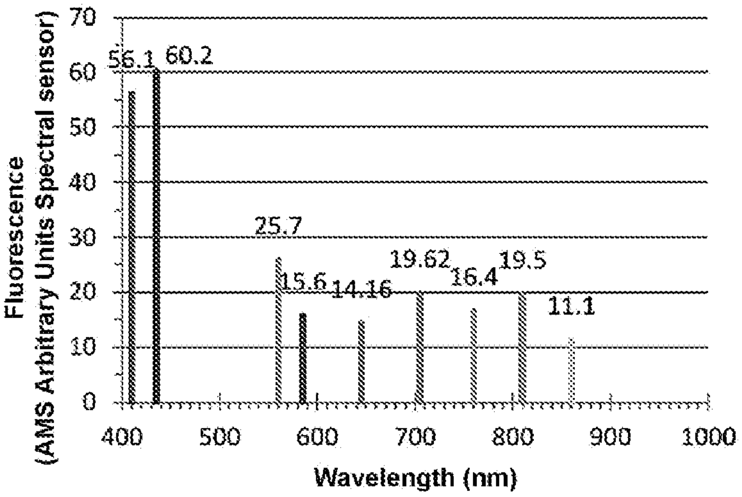
FIG. 1 shows a histogram showing the 9 fluorescence intensities of the sample of milk according to Example 1.

The present invention relates to a method for the quantification of Aflatoxin M1 (AFM1) in milk, comprising the steps of a) providing a sample of milk; b) irradiating the sample of milk of step a) with a first electromagnetic radiation comprising at least one wavelength in the range from 340 to 400 nm; c) detecting a second electromagnetic radiation, emitted by the sample of milk of step b), in the range from 410 to 860 nm; d) selecting at least 9 wavelengths comprised in said range from 410 to 860 nm of the second electromagnetic radiation detected in step c); and e) quantifying the Aflatoxin M1 (AFM1) in said sample of milk, on the basis of the intensity of the radiation emitted at said at least 9 wavelengths selected in step d), wherein said at least 9 wavelengths are selected from the group consisting of 410 nm, 435 nm, 560 nm, 585 nm, 645 nm, 705 nm, 760 nm, 810 nm, and 860 nm; and wherein said at least 9 wavelengths are used to quantify Aflatoxin M1 (AFM1), by means of equation (1):

$$AFM1(ppt) = 0.0092 \times (F1)^2 + 1.0694 \times (F1) + 31.635 \quad (1)$$

wherein AFM1 (ppt) is the concentration of Aflatoxin M1 in said sample of milk in ng $kg^{-1}$, and F1 is a parameter calculated by means of equation (II):

$$F1 = 2.533 \times Is_{410nm} + -0.132 \times Is_{435nm} + 5.527 \times Is_{560nm} + 1.911 \times Is_{535nm} + 7.225 \times Is_{645nm} + -1.082 \times Is_{705nm} + -8.849 \times Is_{760nm} + -11.337 \times Is_{810nm} + 1.874 \times Is_{860nm}, \quad (II)$$

and wherein $Is_{410\ nm}$, $Is_{435\ nm}$, $Is_{560\ nm}$, $Is_{585\ nm}$, $Is_{645\ nm}$, $Is_{705\ nm}$, $Is_{760\ nm}$, $Is_{810\ nm}$, $Is_{860nm}$ are the standardized fluorescence intensity values, respectively at 410 nm, 435 nm, 560 nm, 585 nm, 645 nm, 705 nm, 760 nm, 810 nm, and 860 nm, wherein said standardized fluorescence intensity values are respectively obtained according to the following equations (III1-III9):

$$Is_{410nm} = (I_{410nm} - 52.737)/2.468 \quad (III1)$$

$$Is_{435nm} = (I_{435nm} - 52.503)/2.141 \quad (III2)$$

$$Is_{560nm} = (I_{560nm} - 24.267)/0.928 \quad (III3)$$

$$Is_{585nm} = (I_{585nm} - 14.800)/0.563 \quad (III4)$$

$$Is_{645nm} = (I_{645nm} - 13.437)/0.523 \quad (III5)$$

$$Is_{705nm} = (I_{705nm} - 18.540)/0.759 \quad (III6)$$

$$Is_{760nm} = (I_{760nm} - 20.033)/2.972 \quad (III7)$$

$$Is_{810nm} = (I_{810nm} - 24.233)/4.183 \quad (III8)$$

$$Is_{860nm} = (I_{860nm} - 12.387)/1.574 \quad (III9)$$

wherein $I_{410\ nm}$, $I_{435\ nm}$, $I_{560\ nm}$, $I_{585\ nm}$, $I_{645\ nm}$, $I_{705\ nm}$, $I_{760\ nm}$, $I_{810\ nm}$, $I_{860nm}$ are respectively the values of fluorescence intensity detected in phase c), respectively at 410 nm, 435 nm, 560 nm, 585 nm, 645 nm, 705 nm, 760 nm, 810 nm, and 860 nm.

Without being bound to any theory, and as will be apparent from the following and the examples, the inventors believe that by identifying at least 9 specific wavelengths comprised in a range from 410 to 860 nm of the method of the invention, emitted by a sample of milk after irradiation with an electromagnetic radiation comprised in the range from 340 to 400 nm, and on the basis of the intensity of the radiation emitted at said at least 9 specific wavelengths, there is an advantageous possibility of directly and quickly identifying Aflatoxin M1 (AFM1) in a sample of milk, allowing a better and easier identification and quantification of said sample of milk.

In view of this, the present invention provides a simple method, convenient in terms of the cost and time required to perform the analysis, which allows direct, rapid, accurate, and precise quantification of Aflatoxin M1 (AFM1) in a sample of milk.

In the present invention with the following terms:

"photo-derivatization" it is meant a modification reaction of Aflatoxin M1 (AFM1) obtained by irradiation with an electromagnetic radiation comprising the wavelength of 254 nm, to give an Aflatoxin M1 named AFM2a of formula (i):

(i)

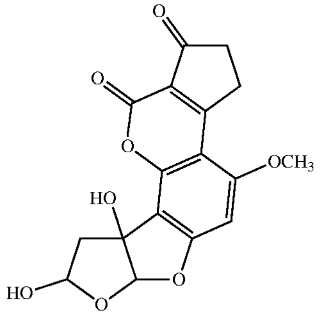

Photo-derivatization allows to increase the intensity of the radiation emitted (fluorescence) by the sample after irradiation (excitation) with an electromagnetic radiation having at least one wavelength comprised in the range from 340 to 400 nm;

"chemical derivatization" it is meant a modification reaction of the Aflatoxin M1 (AFM1) molecule with the addition of groups of atoms, obtained chemically/electrochemically, in order to increase the intensity of the emitted radiation (fluorescence) after irradiation (excitation) with an electromagnetic radiation having at least one wavelength comprised in the range of 340 to 400 nm. This process can be achieved either by hydration of the double bond of the bis-furan unit of Aflatoxin M1 (AFM1) through trifluoroacetic acid, or by saturation of the cis-furan double bond of Aflatoxin M1 (AFM1) with bromination, i.e. formation of new carbon-bromine bonds in the presence of bromine or PBPB (pyridinium bromide perbromide), or by iodination, i.e. formation of carbon-iodine bonds in the presence of iodine.

The method according to the present invention, through the identification at least 9 specific wavelengths comprised in a range from 410 to 860 nm, allows a direct and fast identification and quantification of Aflatoxin M1 (AFM1) in a sample of milk. Said at least 9 wavelengths are selected from the group consisting of 410 nm, 435 nm, 560 nm, 585 nm, 645 nm, 705 nm, 760 nm, 810 nm, and 860 nm, and in step e), said at least 9 wavelengths are used to quantify Aflatoxin M1 (AFM1), by means of equation (I):

$$AFM1(ppt) = 0.0092 \times (F1)^2 + 1.0694 \times (F1) + 31.635 \quad \text{(I)}$$

wherein AFM1 (ppt) is the concentration of Aflatoxin M1 in said sample of milk in ng $kg^{-1}$, and F1 is a parameter calculated by means of equation (II):

$$F1 = 2.533 \times Is_{410nm} + -0.132 \times Is_{435nm} + 5.527 \times Is_{560nm} + 1.911 \times Is_{535nm} + 7.225 \times Is_{645nm} + -1.082 \times Is_{705nm} + -8.849 \times Is_{760nm} + -11.337 \times Is_{810nm} + 1.874 \times Is_{860nm}, \quad \text{(II)}$$

and in cui $Is_{410\ nm}$, $Is_{435\ nm}$, $Is_{560\ nm}$, $Is_{585\ nm}$, $Is_{645\ nm}$, $Is_{705\ nm}$, $Is_{760\ nm}$, $Is_{810\ nm}$, $Is_{860nm}$ are the standardized fluorescence intensity values at 410 nm, 435 nm, 560 nm, 585 nm, 645 nm, 705 nm, 760 nm, 810 nm, and 860 nm, respectively, wherein said standardised fluorescence intensity values are respectively obtained according to the following equations (III1-III9):

$$Is_{410nm} = (I_{410nm} - 52.737)/2.468 \quad \text{(III1)}$$

$$Is_{435nm} = (I_{435nm} - 52.503)/2.141 \quad \text{(III2)}$$

$$Is_{560nm} = (I_{560nm} - 24.267)/0.928 \quad \text{(III3)}$$

$$Is_{585nm} = (I_{585nm} - 14.800)/0.563 \quad \text{(III4)}$$

$$Is_{645nm} = (I_{645nm} - 13.437)/0.523 \quad \text{(III5)}$$

$$Is_{705nm} = (I_{705nm} - 18.540)/0.759 \quad \text{(III6)}$$

$$Is_{760nm} = (I_{760nm} - 20.033)/2.972 \quad \text{(III7)}$$

$$Is_{810nm} = (I_{810nm} - 24.233)/4.183 \quad \text{(III8)}$$

$$Is_{860nm} = (I_{860nm} - 12.387)/1.574 \quad \text{(III9)}$$

wherein $I_{410\ nm}$, $I_{435\ nm}$, $I_{560\ nm}$, $I_{585\ nm}$, $I_{645\ nm}$, $I_{705\ nm}$, $I_{760\ nm}$, $I_{810\ nm}$, $I_{860nm}$ are respectively the values of fluorescence intensity detected in phase c), respectively at 410 nm, 435 nm, 560 nm, 585 nm, 645 nm, 705 nm, 760 nm, 810 nm, and 860 nm.

Advantageously, in the method according to the present invention said sample of milk is a sample of raw milk.

Even more advantageously, said sample of raw milk is selected from the group consisting of pre-harvest raw milk, bulk milk, whey, and mixtures thereof.

Preferably, the raw milk is selected from the group consisting of raw bovine milk, sheep milk, goat milk, buffalo milk, and mixtures thereof.

In a preferred and advantageous aspect of the invention, at least one step from a) to e) of the method according to the present invention takes place at a temperature comprised in a range from 4 to 37° C. More preferably, all steps from a) to e) of the method according to the present invention take place at a temperature comprised in a range from 4 to 37° C.

In a particularly preferred embodiment of the method according to the invention, the steps from a) to e) take place at a temperature comprised in a range from 15 to 30° C., even more preferably from 22 to 27° C.

Preferably, step a) of the method according to the invention comprises injecting a sample of milk into a container apt to contain said sample of milk.

In a further preferred and advantageous aspect of the invention, step a) of the method of the invention comprises a step a') of irradiating with a third electromagnetic radiation comprising at least one wavelength in the range from 200 to 280 nm.

Even more preferably, in step a') of irradiating, the third electromagnetic radiation comprises at least a wavelength of 254 nm.

Still preferably, said step a') of irradiating has a duration of at least 1 minute, more preferably it has a duration in the range from 1 to 2 minutes.

In this step a') said third electromagnetic radiation, having at least a wavelength of 254 nm, allows to photo-derivatize Aflatoxin M1 (AFM1) in the sample so as to obtain Aflatoxin M1 named AFM2a of formula (i):

(i)

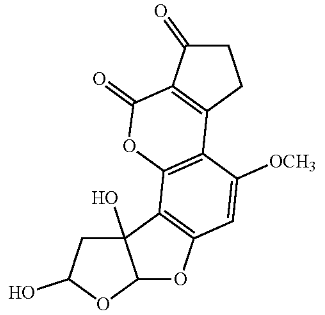

Subsequently, in step b) of the method according to the invention, the sample of milk of step a) is irradiated with a first electromagnetic radiation comprising at least a wavelength in the range from 340 to 400 nm.

Preferably, said first radiation comprises at least a wavelength of 365 nm.

Advantageously, in step b) of the method according to the invention, the irradiation has a duration of at least 1 minute, more preferably it has a duration in the range from 1 to 2 minutes.

In a further preferred and advantageous aspect, step a) of the method of the invention comprises a step a") of adding trifluoroacetic acid, at least a source of bromine selected from the group consisting of alkali bromine salts, and PBPB (pyridinium bromide-perbromide), or iodine, or mixtures thereof.

In this step a") said addition allows for a chemical derivatization which enables to increase the intensity of the emitted radiation (fluorescence) when subjected to irradiation with the first electromagnetic radiation of step b) of the method according to the present invention.

Advantageously, after irradiation with a first electromagnetic radiation of step b) of the method of the invention, there is a step c) of detecting a second electromagnetic radiation, emitted by the sample of milk of step b), having a wavelength comprised in the range from 410 to 860 nm.

Preferably, said step c) of detecting said second electromagnetic radiation has a duration of at least 5 seconds, more preferably has a duration in the range from 5 to 10 seconds.

Advantageously, a detector is used to detect the radiation emitted in step c). Still advantageously said detector is a spectral sensor.

Figure 4:
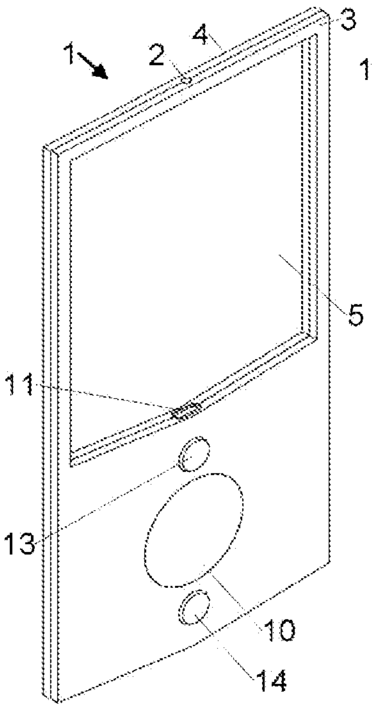
FIG. 4 shows a first axonometric view of the container.
Figure 5:
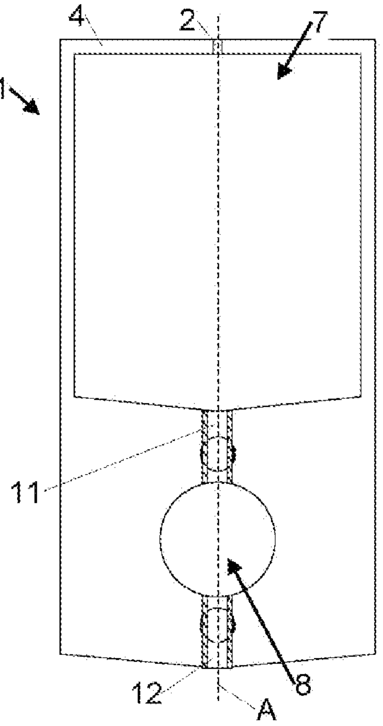
FIG. 5 shows a vertical section of the container of FIG. 4.
Figure 6:
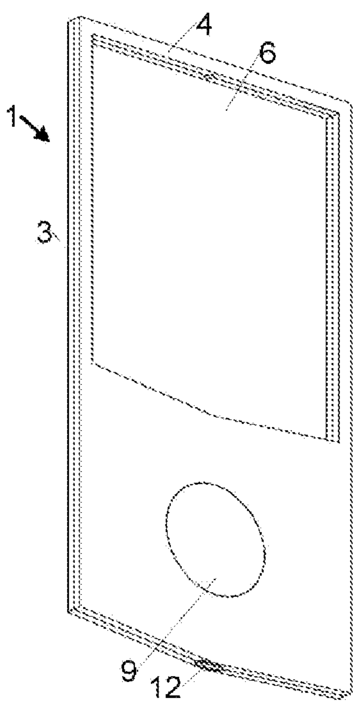
FIG. 6 shows a second axonometric view of the container of FIG. 4.

Referring to FIGS. 4 to 6, it can be seen that the container 1 according to the present description, is provided with at least one inlet duct 2 into which a sample of milk to be analysed can be injected by means of an external apparatus (not shown). The container 1 preferably comprises at least two flat frames 3, 4, in particular having a substantially rectangular shape, each of which is provided with at least one window. A window 5 of the first frame 3 is closed by a transparent slab, while a window 6 of the second frame 4 is closed by a reflective slab from the inside towards the first frame 3, in order to equalize the irradiation of the sample of milk with possible third electromagnetic radiations, and to avoid the dispersion thereof. The window 6 of the second frame 4 is arranged at a distance comprised between 1 and 10 mm in front of the window 5 of the first frame 3. The space between the windows 5, 6 and surrounded by the frames 3, 4 forms an auxiliary chamber 7, in particular having a volume of at least 0.5 mL, preferably 50 mL. The window 5 of the first frame 3 allows the exposure of the content of the auxiliary chamber 7 to an electromagnetic radiation, in particular said third electromagnetic radiation to modify the AFM1 aflatoxin molecule (derivatization), making it more fluorescent in blue wavelengths following subsequent irradiation with said first electromagnetic radiation.

The frames 3, 4 are joined together in a separable way, for example by means of screws, interlocking or at least one hinge arranged on an adjacent side thereof, so as to allow internal cleaning and reuse of the container 1. A thin layer of elastomeric material acting as a seal is applied on the internal side of at least one frame 3 and/or 4 to prevent liquid leakage during use.

At least one main chamber 8 is arranged between the frames 3, 4 below the auxiliary chamber 7. For example, the main chamber 8 has a substantially discoidal shape and is bordered by a transparent window 9 which is derived in the second frame 4.

The volume of the main chamber 8 is preferably smaller, in particular about 5 mL, than the volume of the auxiliary chamber 7, since the main chamber 8 serves to break down the just derivatized sample into sub-samples on which to perform fluorescence measurements, induced by irradiation with the first electromagnetic radiation, for greater statistical robustness of the data obtained.

The main chamber 8 is also bordered by a reflective window 10 which is derived in the first frame 3 and is apt to reflect towards the inside of the main chamber 8 the first electromagnetic radiation, so as to improve the uniformity of the irradiation and maximize the fluorescence of Aflatoxin AFM1 towards the detector.

At least one internal duct 11 connects the auxiliary chamber 7 to the main chamber 8. The base of the auxiliary chamber 7 is slightly inclined towards the internal duct 11 to facilitate the flow of the sample from the auxiliary chamber 7 to the internal duct 11.

At least one outlet duct 12 connects the main chamber 8 with the outside of the container 1.

The internal duct 11 and/or the outlet duct 12 are preferably straight and/or made of an elastomeric material, for example a soft silicone material, with a flattened cross-section.

The internal duct 11 and/or the outlet duct 12 are equipped with at least one valve, for example a piston 13, 14 which is movable in the frame 3 or 4, in particular in the first frame 3, to crush the external surface of the internal duct 11 and/or the outlet duct 12 and thus prevent the passage of at least a portion of the sample from the auxiliary chamber 7 to the main chamber 8 and/or from the main chamber 8 towards the outside of the container 1.

The auxiliary chamber 7, the internal duct 11, the main chamber 8 and the outlet duct 12 are preferably aligned along a common axis A, in particular an axis of symmetry of the container 1.

Figure 7:
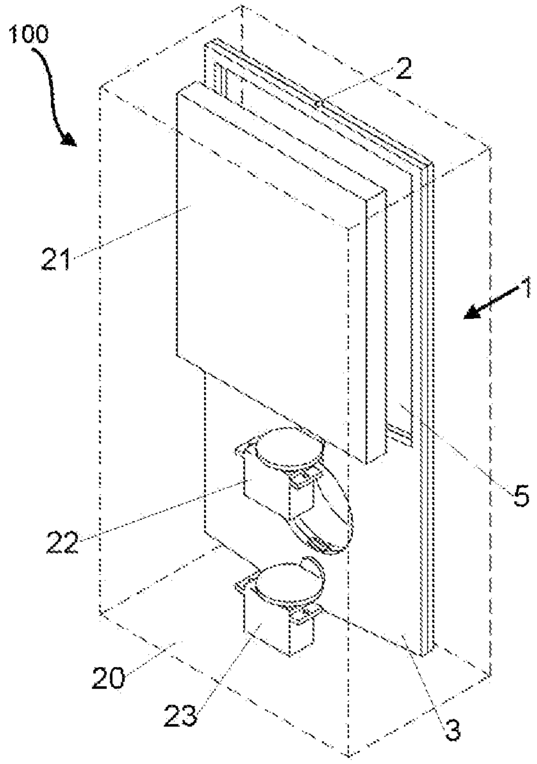
FIG. 7 shows a first schematic axonometric view of the device.
Figure 8:
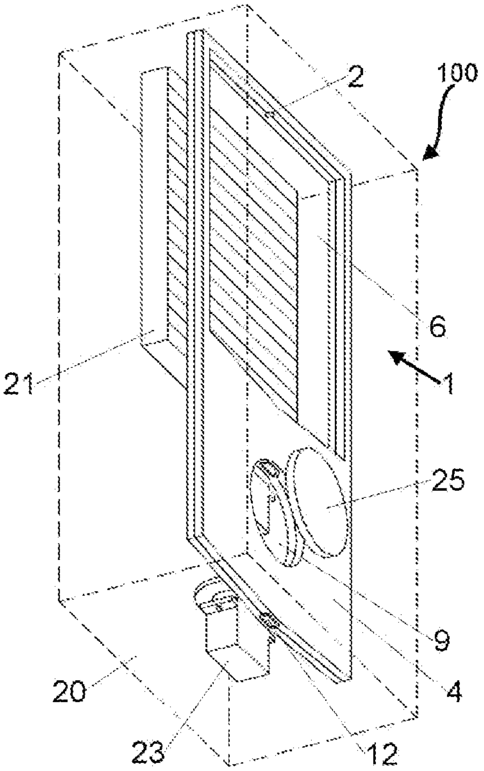
FIG. 8 shows a second schematic axonometric view of the device of FIG. 7.

Referring also to FIGS. 7 and 8, it can be seen that the device 100 according to the present description comprises a casing 20 (shown with dashed lines) and a housing (not shown) apt to removably house at least one container 1 of the type described above, with its common axis A arranged in a substantially vertical manner.

The device 100 may further comprise at least one auxiliary source 21 of a third electromagnetic radiation which is arranged alongside the housing for the container 1 to irradiate the content of the auxiliary chamber 7 of the container 1, in particular through the window 5 of the first frame 3. The auxiliary source 21 is preferably provided with a diffuser to equalize the irradiation of the auxiliary chamber 7. The electromagnetic radiations emitted by the auxiliary source 21, after passing through the auxiliary chamber 7, are reflected by the window 6 inwardly.

The third electromagnetic radiations emitted by the auxiliary source 21 have at least one wavelength in the range from 200 to 280 nm, in particular 254 nm. The device 100 further comprises one or more electromechanical actuators 22, 23 which are arranged alongside the housing for the container 1 to open or close the internal duct 11 or the outlet duct 12. The actuators 22, 23 preferably comprise a servomotor apt to rotate a cam that can press a piston 13, 14 of the container 1.

The rotation of the actuator cam 22 or 23 presses the piston 13 or 14 against the duct 11 or 12, closing its internal lumen and interrupting the passage of the sample. A further rotation of the cam releases the piston 13 or 14 so that the duct 11 or 12 opens due to its elasticity.

Figure 9:
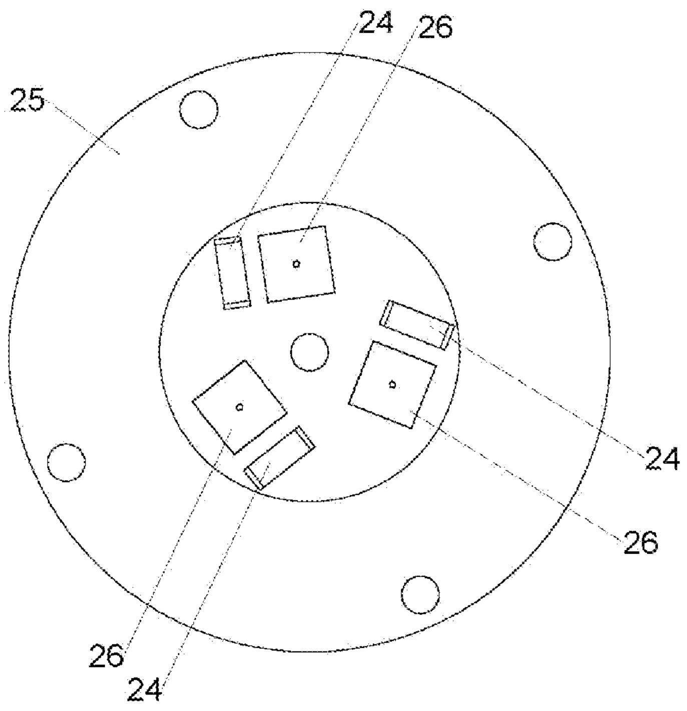
FIG. 9 shows a front view of the first electromagnetic radiation source holder and the device detector of FIG. 7.
Figure 10:
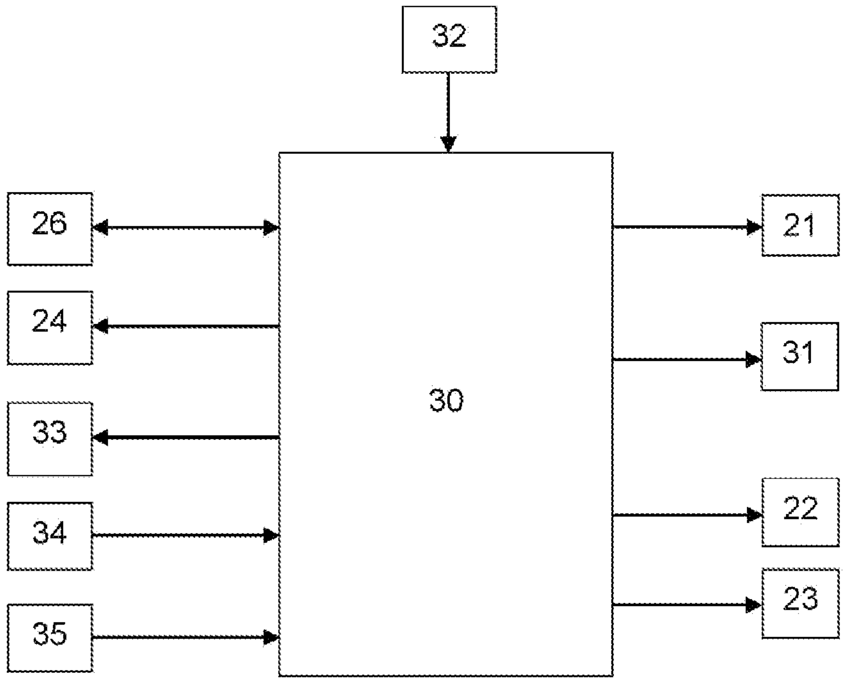
FIG. 10 shows a block diagram of the device in FIG. 7.

Referring also to FIG. 9, it can be seen that the device further comprises at least one main source 24 of first electromagnetic radiations which is arranged alongside the housing for the container 1 to irradiate the content of the main chamber 8 of the container 1, in particular through the transparent window 9 of the second frame 4.

In particular, three main sources 24 are arranged like a triangle on a support 25, for example a printed circuit board, which is arranged alongside the housing for the container 1.

The first electromagnetic radiation emitted by the main sources 24 comprises at least one wavelength in the range of 340 to 400 nm, in particular 365 nm, so as to be able to excite the fluorescence at 435 nm wavelength of Aflatoxin M1 (AFM1), previously derivatized by the auxiliary source 21.

The first electromagnetic radiations emitted by the main sources 24, after passing through the main chamber 8, are reflected by the window 10 inwardly.

The device 100 also comprises at least one spectral sensor 26, in particular a spectral sensor with at least 9 detection wavelengths comprising three integrated circuits arranged like a triangle, such as for example the AMS AG model AS7265x spectral sensor with 18 channels.

The operations of filling the chambers 7, 8, of activating the sources 21, 24 and/or of detecting and controlling the spectral sensor 26 are preferably managed by an electronic control unit 30 provided with a program, in particular executable by a microcontroller, also of a known type, to perform said operations and/or to record on at least one memory 31 the data collected and/or to transfer said data to an external unit, for example a PC, for their subsequent processing and/or display. The control unit 30 is powered by a power source 32, such as a power supply and/or a battery, and may comprise output means 33 and/or input means 34, for example embedded in a touch screen. Thanks to the program of the control unit 30, the device 100 can carry out all the steps of the method described above, manually and/or automatically.

The spectral sensor 26 can simultaneously detect in the main chamber 8 the emission intensity (fluorescence) at 18 wavelengths from a sample of milk, and/or continuously in the range of 410 to 860 nm.

In use, the initially empty container 1 is placed in the housing of the device 100. The control unit 30, after verifying the correct insertion and positioning of the container 1 in the device 100, for example by means of mechanical sensors 35 arranged in the housing of the container 1, closes the internal duct 11 and the outlet duct 12 by operating the actuators 22, 23.

The auxiliary chamber 7 of the container 1 is then filled with a sample of milk through the inlet duct 2, whereupon the control unit 30 activates the auxiliary source 21 to irradiate this sample for a predetermined duration, for example 1-2 minutes, which may be adjustable via the input means 34 and the control unit 30.

After this time has elapsed, the auxiliary source 21 is turned off and the control unit 30 opens the internal duct 11 by means of the actuator 22, so as to fill, by gravity, the main chamber 8 of the container with a first portion of the sample present in the auxiliary chamber 7. During this step, the outlet duct 12 remains closed.

Once the main chamber 8 contains such first portion of the sample (sub-sample), the control unit 30 activates the main sources 24 with a predetermined intensity.

The fluorescence intensity of the sample of milk irradiated by the main sources 24 is detected by the spectral sensor 26 and recorded in the memory 31 of the control unit 30. Having performed such sub-sample analysis, the control unit 30 closes the internal duct 11 and opens the outlet duct 12 to discharge this sub-sample to the outside of the device 100.

The control unit 30 may perform such analysis of various portions of the sample for one or more times, for example 10 times, after which the container 1 may be removed from the device 100, opened and washed with water and detergent.

The invention will be further detailed with the following experimental part, which sets forth examples and tests of the method of the invention.

EXPERIMENTAL PART

Example 1

Determination of the Amount of Aflatoxin M1 (AFM1) in a Sample of Milk According to the Method of the Invention A sample was prepared, starting from 50 mL of milk, collected from dairy cattle farms in Veneto, free of Aflatoxin M1 (AFM1), adding to said 50 mL of milk, an amount of 22.5 μL of an aqueous solution having a concentration of 200000 ppt of AFM1, obtaining a sample with a known concentration of Aflatoxin M1 (AFM1) equal to 90 ppt of AFM1.

The aforesaid sample of milk was subjected to photoderivatization for 2 minutes with an electromagnetic radiation, generated by a mercury vapour lamp, having a wavelength comprised between 200 and 280 nm and a peak at 254 nm.

The sample of milk was then irradiated for 2 minutes at a temperature of 25° C. with an electromagnetic radiation, generated by a Wood's light lamp, having a wavelength in the range from 340 to 400 nm and a peak at 365 nm.

By using the device according to the present description, while keeping the excitation source (Wood's light) active, fluorescence intensity values were acquired at the wavelengths of 410 nm, 435 nm, 560 nm, 585 nm, 645 nm, 705 nm, 760 nm, 810 nm, and 860 nm.

FIG. 1 shows the histogram with the 9 fluorescence intensities of the sample of milk tested.

Table 1 reports the acquired fluorescence intensity and standardized fluorescence intensity values calculated according to equations (III1-III9).

TABLE 1

| Wavelength (nm) | Fluorescence intensity (AMS arbitrary units) | Standardized fluorescence intensity |
|---|---|---|
| 410 | 56.1 | 1.363 |
| 435 | 60.2 | 3.595 |
| 560 | 25.7 | 1.544 |
| 585 | 15.6 | 1.420 |
| 645 | 14.16 | 1.383 |
| 705 | 19.62 | 1.424 |
| 760 | 16.4 | −1.223 |
| 810 | 19.5 | −1.132 |
| 860 | 11.1 | −0.818 |

Said standardized fluorescence intensity values were then used to calculate the F1 parameter according to equation (II):

$$F1=(2.533\times1.363)+(-0.132\times3.595)+(5.527\times1.544)+(1.911\times1.420)+(7.225\times1.383)+(-1.082\times1.424)+(-8.849\times-1.223)+(-11.337\times-1.132)+(1.874\times-0.818)=44.797.$$

Subsequently, the concentration of Aflatoxin M1 (AFM1) in the sample of milk was calculated using equation (I).

$$\text{AFM1 (ppt)}=0.0092\times(44.797)^2+1.0694\times(44.797)+31.635=98.003\text{ ppt.}$$

It is evident that the method according to the invention is able to quantify the concentration of Aflatoxin M1 (AFM1) in a sample of milk by obtaining a value extremely close to the actual value of 90 ppt.

Example 2

Determination of the Amount of Aflatoxin M1 (AFM1) in a Sample of Milk According to the Method of the Invention with Comparison with Known HPLC Method (Mortimer et al., 1987)

A 50 mL sample of milk collected from dairy cattle farms in Veneto was provided. Said sample of milk was subjected to analysis according to the known method (Mortimer et al., 1987) coupled with HPLC and a concentration of 52 ppt of Aflatoxin M1 (AFM1) was measured.

The aforesaid sample of milk was subjected to photo-derivatization for 2 minutes with an electromagnetic radiation generated by a mercury vapour lamp, having a wavelength comprised between 200 and 280 nm and a peak at 254 nm.

Said sample of milk was then irradiated for 2 minutes at a temperature of 25° C. with an electromagnetic radiation, generated by a Wood's light lamp, having a wavelength in the range from 340 to 400 nm and a peak at 365 nm.

By using the device according to the present description, while keeping the excitation source (Wood's light) active, fluorescence intensity values were acquired at the wavelengths of 410 nm, 435 nm, 560 nm, 585 nm, 645 nm, 705 nm, 760 nm, 810 nm, and 860 nm.

Figure 2:
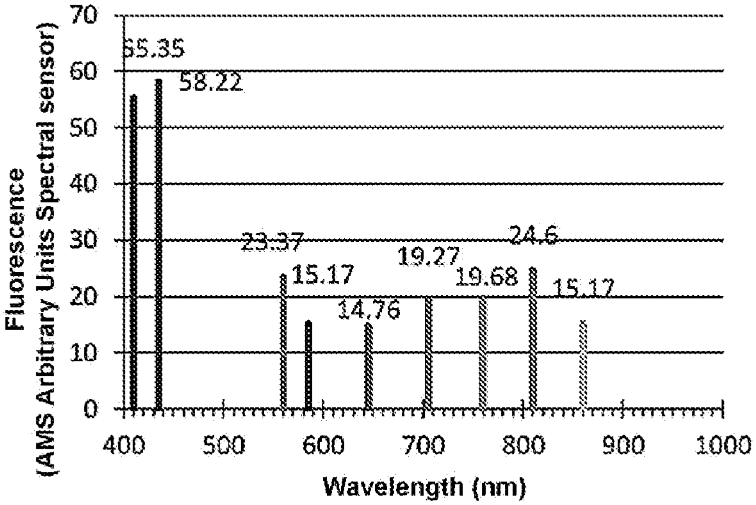
FIG. 2 shows a histogram showing the 9 fluorescence intensities of the sample of milk according to Example 2.

FIG. 2 shows the histogram with the 9 fluorescence intensities of the sample of milk tested.

Table 2 reports the acquired fluorescence intensity and standardized fluorescence intensity values calculated according to equations (III1-III9).

TABLE 2

| Wavelength (nm) | Fluorescence intensity (AMS arbitrary units) | Standardized fluorescence intensity |
|---|---|---|
| 410 | 55.35 | 1.059 |
| 435 | 58.22 | 2.670 |
| 560 | 23.37 | −0.966 |
| 585 | 15.17 | 0.657 |
| 645 | 14.76 | 2.531 |
| 705 | 19.27 | 0.962 |
| 760 | 19.68 | −0.119 |
| 810 | 24.6 | 0.088 |
| 860 | 15.17 | 1.768 |

Said standardized fluorescence intensity values were then used to calculate the F1 parameter according to equation (II):

$$F1=(2.533\times1.059)+(-0.132\times2.670)+(5.527\times-0.966)+(1.911\times0.657)+(7.225\times2.531)+(-1.082\times0.962)+(-8.849\times-0.119)+(-11.337\times-0.088)+(1.874\times1.768)=18.862.$$

Subsequently, the concentration of AFM1 in the sample of milk was calculated using equation (I).

$$\text{AFM1 (ppt)}=0.0092\times(18.862)^2+1.0694\times(18.862)+31.635=55.079\text{ ppt.}$$

The concentration values of Aflatoxin M1 (AFM1), obtained by means of the method of the invention, were compared to those obtained by means of the known method (Mortimer et al., 1987) coupled with HPLC.

It is evident that the method according to the invention is able to quantify the concentration of Aflatoxin M1 (AFM1) in a sample of milk obtaining a value extremely close to the value obtained according to the known method (Mortimer et al., 1987) coupled with HPLC.

Example 3

Determination of the Amount of Aflatoxin M1 (AFM1) in a Sample of Milk According to the Method of the Invention with Comparison with Known HPLC Method (Mortimer et al., 1987)

A 50 mL sample of milk collected from dairy cattle farms in Veneto was provided. Said sample of milk was subjected to analysis according to the known method (Mortimer et al., 1987) coupled with HPLC and a concentration of 8 ppt of Aflatoxin M1 (AFM1) was measured.

The aforesaid sample of milk was subjected to photo-derivatization for 2 minutes with an electromagnetic radiation generated by a mercury vapour lamp, having a wavelength comprised between 200 and 280 nm and a peak at 254 nm.

The sample of milk was then irradiated for 2 minutes at a temperature of 25° C. with an electromagnetic radiation, generated by a Wood's light lamp, having a wavelength in the range from 340 to 400 nm and a peak at 365 nm.

By using the device according to the present description, while keeping the excitation source (Wood's light) active, fluorescence intensity values were acquired at the wavelengths of 410 nm, 435 nm, 560 nm, 585 nm, 645 nm, 705 nm, 760 nm, 810 nm, and 860 nm.

Figure 3:
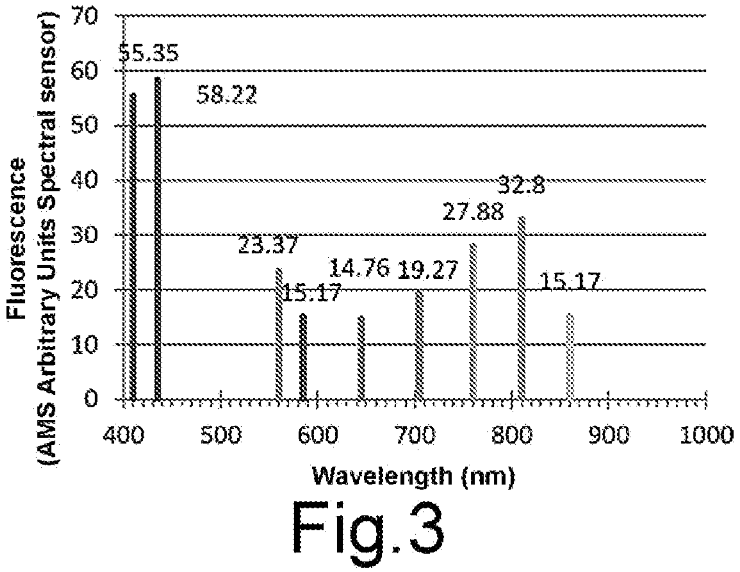
FIG. 3 shows a histogram showing the 9 fluorescence intensities of the sample of milk according to Example 3.

FIG. 3 shows the histogram with the 9 fluorescence intensities of the sample of milk tested.

Table 3 reports the acquired fluorescence intensity and standardized fluorescence intensity values calculated according to equations (III1-III9).

TABLE 3

| Wavelength (nm) | Fluorescence intensity (AMS arbitrary units) | Standardized fluorescence intensity |
|---|---|---|
| 410 | 55.35 | 1.059 |
| 435 | 58.22 | 2.67 |
| 560 | 23.37 | −0.966 |
| 585 | 15.17 | 0.657 |
| 645 | 14.76 | 2.531 |
| 705 | 19.27 | 0.962 |
| 760 | 27.88 | 2.641 |
| 810 | 32.8 | 2.048 |
| 860 | 15.17 | 1.768 |

Subsequently, the parameter F1 was calculated using equation (II):

$$F1=(2.533\times1.059)+(-0.132\times2.67)+(5.527\times-0.966)+(1.911\times0.657)+(7.225\times2.531)+(-1.082\times0.962)+(-8.849\times2.641)+(-11.337\times2.048)+(1.874\times1.768)=-27.782.$$

Subsequently, the concentration of AFM1 in the sample of milk was calculated using equation (I).

$$\text{AFM1 (ppt)}=0.0092\times(-27.782)^2+1.0694\times(-27.782)+31.635=9.026\text{ ppt.}$$

The concentration values of Aflatoxin M1 (AFM1), obtained by means of the method of the invention, were compared to those obtained by means of the known method (Mortimer et al., 1987) coupled with HPLC.

It is evident that the method according to the invention is able to quantify the concentration of Aflatoxin M1 (AFM1) in a sample of milk obtaining a value extremely close to the value obtained according to the known method (Mortimer et al., 1987) coupled with HPLC.

Any variants or additions may be made by the persons skilled in the art to the embodiments described and illustrated herein while remaining within the scope of the following claims. In particular, further embodiments may comprise the technical characteristics of any of the following claims with the addition of one or more technical characteristics described in the text or illustrated in the drawings, taken singularly or in any combination thereof.

The invention claimed is:

1. A method for the quantification of Aflatoxin M1 (AFM1) in milk, comprising the steps of:

a) providing a sample of milk;

a') irradiating the sample of milk with an electromagnetic radiation comprising at least one wavelength in a range from 200 to 280 nm, suitable to photo-derivatize Aflatoxin M1 (AFM1) so as to obtain photo-derivatized Aflatoxin M1 (AFM2a);

a") adding trifluoroacetic acid, or at least one source of bromine selected from the group consisting of alkali bromine salts and pyridinium bromide-perbromide (PBPB), or iodine, and mixtures thereof, to the sample of milk obtained in step a') so as to chemically derivatize Aflatoxin M1 and increase fluorescence emission;

b) irradiating the sample of milk obtained in the step a") with an electromagnetic radiation comprising at least one wavelength in a range from 340 to 400 nm;

c) detecting a second electromagnetic radiation emitted by the sample of milk in response to the irradiation of step b), said second electromagnetic radiation being detected in a wavelength range from 410 to 860 nm;

d) selecting fluorescence intensity values detected at the following wavelengths of the second electromagnetic radiation: 410 nm, 435 nm, 560 nm, 585 nm, 645 nm, 705 nm, 760 nm, 810 nm, and 860 nm;

e) calculating standardized fluorescence intensity values Is410 nm, Is435 nm, Is560 nm, Is585 nm, Is645 nm, Is705 nm, Is760 nm, Is810 nm and Is860 nm according to the following equations (III1-III9):

$$Is410\text{nm} = (I410\text{nm} - 52.737)/2.468 \quad \text{(III1)}$$

$$Is435\text{nm} = (I435\text{nm} - 52.503)/2.141 \quad \text{(III2)}$$

$$Is560\text{nm} = (I560\text{nm} - 24.267)/0.928 \quad \text{(III3)}$$

$$Is585\text{nm} = (I585\text{nm} - 14.800)/0.563 \quad \text{(III4)}$$

$$Is645\text{nm} = (I645\text{nm} - 13.437)/0.523 \quad \text{(III5)}$$

$$Is705\text{nm} = (I705\text{nm} - 18.540)/0.759 \quad \text{(III6)}$$

$$Is760\text{nm} = (I760\text{nm} - 20.033)/2.972 \quad \text{(III7)}$$

$$Is810\text{nm} = (I810\text{nm} - 24.233)/4.183 \quad \text{(III8)}$$

$$Is860\text{nm} = (I860\text{nm} - 12.387)/1.574 \quad \text{(III9)}$$

wherein I410 nm, I435 nm, I560 nm, I585 nm, I645 nm, I705 nm, I760 nm, I810 nm and I860 nm are fluorescence intensity values detected in step c);

f) calculating a parameter F1 according to the following equation (II): and

F1=2.533× Is410 nm−0.132×Is435 nm+5.527× Is560 nm+1.911× Is585 nm+7.225× Is645 nm−1.082× Is705 nm−8.849× Is760 nm−11.337× Is810 nm+1.874×Is860 nm (II);

g) quantifying a concentration of Aflatoxin M1 (AFM1) in the sample of milk by applying the following equation (I):

$$AFM1(ppt) = 0.0092\times(F1)^2 + 1.0694\times(F1) + 31.635 \quad \text{(I)}$$

wherein AFM1 (ppt) is the concentration of Aflatoxin M1 expressed in ng $kg^{-1}$.

2. The method according to claim 1, wherein said sample of milk is a sample of raw milk.

3. The method according to claim 1, wherein at least one step from a) to c) occurs at a temperature in a range from 4 to 37° C.

4. The method according to claim 1, wherein step a) comprises injecting the sample of milk into a container.

5. The method according to claim 1, wherein step a') of irradiating has a duration of at least 1 minute.

6. The method according to claim 1, wherein step b) of irradiating has a duration of at least 1 minute.

7. The method according to claim 1, wherein the step c) of detecting has a duration of at least 5 seconds.

8. A device (100) for analyzing at least one sample of milk, comprising:

at least one main source (24) configured to irradiate the at least one sample with a first electromagnetic radiation comprising at least one wavelength in a range from 340 to 400 nm, at least one spectral sensor (26) configured to detect a second electromagnetic radiation, emitted by the at least one sample, in a range from 410 to 860 nm;

a container (1) configured to contain the at least one sample of milk, having one or more electromechanical actuators (22, 23) configured to open and close one or more ducts (11, 12) of said container (1); and an electronic control unit (30) configured to perform, by means of the device (100), manually and/or automatically, the method according to claim 1.

9. The device (100) according to claim 8, further comprising an auxiliary source (21) configured to irradiate the at least one sample with a third electromagnetic radiation comprising at least one wavelength in a range from 200 to 280 nm.

10. The device (100) according to claim 8, wherein said container (1) comprises an auxiliary chamber (7) provided with at least one inlet duct (2) for introducing a sample of milk and at least a first window (5) configured to allow the irradiation of the sample in the auxiliary chamber (7) with an electromagnetic radiation emitted by a source (21) placed outside the container (1), wherein the auxiliary chamber (7) is connected via at least one internal duct (11) to a main chamber (8) provided with at least a second window (9) configured to allow the irradiation of the sample in the main chamber (8) with an electromagnetic radiation emitted by the at least one main source (24) placed outside the container (1), wherein the main chamber (8) is connected to an outlet duct (12) for discharging the sample of milk.

11. The device (100) according to claim 10, wherein the first window (5) and the second window (9) are derived in a first flat frame (3) and/or in a second flat frame (4), wherein the frames (3, 4) are joined together in a separable way.

12. The device (100) according to claim 11, wherein one or both frames (3, 4) comprise several windows (5, 6, 9, 10).

13. The device (100) according to claim 12, wherein the surface of a window (6, 10) of at least one frame (3, 4), which faces towards the first window (5) or the second window (9) of the other frame (3, 4), is reflective.

14. The device (100) according to claim 10, wherein the at least one internal duct (11) and/or the outlet duct (12) are equipped with at least one valve (13, 14).

15. The device (100) according to claim 10, wherein the auxiliary chamber (7), the at least one internal duct (11), the main chamber (8) and the outlet duct (12) are aligned along a common axis (A).

16. The device (100) according to claim 10, wherein said container (1) is housed in a housing of the device in a removable way.

17. The method according to claim 1, wherein in step a') said radiation comprises a wavelength of 254 nm.

* * * * *